(12) United States Patent
Navran, Jr.

(10) Patent No.: US 7,507,581 B2
(45) Date of Patent: Mar. 24, 2009

(54) INHIBITION OF PANCREATIC ISLET AGGREGATION

(75) Inventor: Stephen S. Navran, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 345 days.

(21) Appl. No.: 11/396,437

(22) Filed: Apr. 3, 2006

(65) Prior Publication Data

US 2006/0246582 A1  Nov. 2, 2006

Related U.S. Application Data

(60) Provisional application No. 60/677,642, filed on May 4, 2005, provisional application No. 60/668,294, filed on Apr. 5, 2005.

(51) Int. Cl.
*C12N 5/02* (2006.01)
*C12N 5/08* (2006.01)

(52) U.S. Cl. .................. 435/391; 435/366; 435/383; 435/384; 435/394

(58) Field of Classification Search .................. None
See application file for complete search history.

(56) References Cited

U.S. PATENT DOCUMENTS 5,211,657 A  5/1993  Yamada et al.

OTHER PUBLICATIONS

Jiang et al "Laminin-1 Promotes Differentiation of Fetal Mouse Pancreatic .beta.-Cells" Diabetes, Apr. 1999, vol. 48, pp. 722-730.*
Murdoch et al "Methods of human islet culture for transplantation," Cell Transplantation, 2004, vol. 13, No. 6, pp. 605-617.*
Best, Leonard. ""Pancreatic Beta-Cells"." Endocrine Cell Culture. Ed. Steven Bidley. Cambridge: The Cambridge University Press, 1998, (pp. 65-67 provided).*
Paraskevas S, Duguid WP, Maysinger D, Feldman L, Agapitos D, Rosenberg L. Apoptosis occurs in freshly isolated human islets under standard culture conditions. Transplant. Proc. 29:750-752, 1997.
Cattan P, Berney T, Schena S, Molano RD, Pileggi A, Vizzardelli C, Ricordi C, Iverardi L. Early assessment of apoptosis in isolated islets of Langerhans. Transplantation 71:857-862, 2001.
Gaber OA, Fraga DW, Callicutt CS, Gerlling IC, Sabek OM, Kotb M. Improved in vivo pancreatic islet function after prolonged in vitro islet culture. Transplantation 72:1730-1736, 2001.
Rutzky LP, Bilinski S, Kloc M, Phan T, Zhang H, Katz SM, Stepkowski SM. Microgravity culture condition reduces immunogenicity and improves function of pancreatic islets. Transplantation 74:13-21, 2002.
Rutzky LP, Kloc M, Bilinski S, Phan T, Zhang H, Stepkowski SM, Katz S. Microgravity culture conditions decrease immunogenicityl but maintain excellent morphology of pancreatic islets. Transplant. Proc. 33: 388, 2001.
Deijnen JHM, Hulstaert G, Wolters HJ, Schilfgaarde R. Significance of the peri-insular extracellular matrix for islet isolation from the pancreas of rat, dog, pig and man. Cell Tissue Res 267: 139-146, 1992.
Thomas FT, Contreras JL, Bilbao G, Ricordi C, Curiel D, Thomas JM. Anoikis, extracellular matrix and apoptosis factors in isolated cell transplantation. Surgery 126: 299-304, 1999.
Cameron DF, Hushen JJ, and Nazian SJ. Formation of Insulin-Secreting, Sertoli-Enriched Tissue Constructs by Microgravity Cocultures of Isolated Pig Islets and Rat Sertoli cells. In Vitro Cell Dev Biol Anim 37:490-8, 2001.
Bosco D, Meda P, Halban A, Rouiller, G. Importance of cell-matrix interactions in rat islet b cell secretion in vitro. Diabetes 49:233-243, 2000.
Kleinman HK, Weeks BS, Cannon FB, Sweeney TM, Sephel GC, Clement B, Zain M, Olson MOJ, Jucker M, Burrous BA. Identification of a 110 kDa Nonintegrin Cell Surface Laminin-Binding Protein Which Recognizes and A Chain Neurite-Promoting Peptide. Arch Biochem Biophys 290:320-325, 1991.
Chalazonitis A, Tennyson VM, Kibbey MC, Rothman TP, Gershon MD. The a1 Subunit of Laminin-1 Promotes the Development of Neurons by interacting with LBP110 Expressed by Neural Crest-Derived Cells Immunoselected from the Fetal Mouse Gut. J Neurobiol 33:118-138, 1997.
Brandhorst D, Brandhorst H, Hering BJ, Federlin K, Bretzel RG. Large variability of the intracellular ATP content of human islets isolated from different donors. J. Mol. Med. 77: 93-95, 1999.

* cited by examiner

*Primary Examiner*—L Blaine Lankford
*Assistant Examiner*—Allison M. Ford
(74) *Attorney, Agent, or Firm*—Elizabeth R. Hall

(57) ABSTRACT

A method for improving the health and viability of pancreatic islets and improving the outcome of pancreatic islet transplantations is described. The method includes incubating the islets with an IKVAV-containing laminin A chain peptide, such as PA22-2, either before or during the culturing of the islets in an RCCS bioreactor.

11 Claims, 3 Drawing Sheets

SEQUENCE LISTING

<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: laminin A chain
<300> PUBLICATION INFORMATION:
<301> AUTHORS: Hynda K. Kleinman, Benjamin S. Weeks, Frances B. Cannon,
      Thomas M. Sweeney, Gregory C. Sephel, Bruno Clement, Mona Zain,
      Mark O. J. Olson, Mathias Jucker, and Beth A. Burrous
<302> TITLE: Identification of a 110-kDa Nonintegrin Cell surface
      laminin-Binding Protein Which Recognizes an A Chain
      Neurite-Promoting Peptide
<303> JOURNAL: Archives of Biochemistry and Biophysics
<304> VOLUME: 290
<305> ISSUE: 2
<306> PAGES: 320-25
<307> DATE: 1991-11-01
<313> RELEVANT RESIDUES: (2091)..(2108)
<300> PUBLICATION INFORMATION:
<313> RELEVANT RESIDUES: (2091)..(2108)
<300> PUBLICATION INFORMATION:
<302> TITLE: Laminin A Chain Deduced Amino Acid Sequence, Expression
      Vectors and Active Synthetic Peptides
<310> PATENT DOCUMENT NUMBER: US 5,211,657
<311> PATENT FILING DATE: 1988-11-07
<312> PUBLICATION DATE: 1993-05-18
<313> RELEVANT RESIDUES: (2091)..(2108)

<400> SEQUENCE: 1

Cys Ser Arg Ala Arg Lys Gln Ala Ala Ser Ile Lys Val Ala Val Ser
1               5                   10                  15

Ala Asp Arg

<210> SEQ ID NO 2
<211> LENGTH: 5
<212> TYPE: PRT
<213> ORGANISM: Artificial Sequence
<220> FEATURE:
<223> OTHER INFORMATION: peptide sequence of the LBP 110-binding domain
<300> PUBLICATION INFORMATION:
<301> AUTHORS: Alcmene Chalazonitis, Virginia M. Tennyson, Maura C.
      Kibbey, Taube P. Rothman, Michael D. Gershon
<302> TITLE: The alpha1 Subunit of Laminin-1 Promotes the Development of
      Neurons by Interacting with LBP110 Expressed by Neural
      Crest-Derived Cells Immunoselected from the Fetal Mouse Gut
<303> JOURNAL: J Neurobiol.
<304> VOLUME: 33
<305> ISSUE: 2
<306> PAGES: 118-38
<307> DATE: 1997-08-01
<313> RELEVANT RESIDUES: (2101)..(2105)

<400> SEQUENCE: 2

Ile Lys Val Ala Val
1               5

INHIBITION OF PANCREATIC ISLET AGGREGATION

CROSS REFERENCE TO RELATED APPLICATIONS

This application claims priority to pending U.S. patent application Ser. No. 60/668,294 filed Apr. 5, 2005 by inventor Stephen S. Navran, Jr. entitled "Inhibition of Pancreatic Islet Aggregation" and to pending U.S. patent application Ser. No. 60/677,642 filed May 4, 2005 by inventor Stephen S. Navran, Jr. entitled "Inhibition of Pancreatic Islet Aggregation." The entire text of the above-referenced disclosures is incorporated by reference herein.

BACKGROUND OF THE INVENTION

1. Field of the Invention

The present invention relates to a method for improving the rate of successful pancreatic islet transplantation. More particularly, the present invention relates to a method for maintaining high densities of pancreatic islets in culture.

2. Description of the Related Art

The conventional treatment of type I diabetes with intensive insulin regimens using insulin injections or insulin pumps has resulted in limited success in the long-term treatment of diabetics. Pancreatic islet replacement has been promoted as offering a "cure" for diabetes. Successful islet transplantation has been vigorously pursued for its potential in the complete control of glucose (i.e. a system with balanced glucose sensing and insulin secretion).

In the past, most islet transplants failed to achieve long-term insulin independence for the patient. Islet transplants have been faced with problems associated with the isolation and preservation of pancreatic islets. Several studies have reported that graft failure is related to reduced islet viability due to increased apoptosis of the islets stimulated by mechanical and enzymatic damage during the isolation of the islets (Paraskevas, S., et al. Apoptosis occurs in freshly isolated human islets under standard culture conditions, *Transplant. Proc.* 29:750-752, 1997; Cattan, P., et al. Early assessment of apoptosis in isolated islets of Langerhans. *Transplantation* 71:857-862, 2001).

In 2001, Gaber et al. showed that culturing islets in a serum-free media for one month allowed the islets to recover from the trauma caused by the isolation process and improved islet graft survival after transplantation (Gaber, et al. Improved in vivo pancreatic islet function after prolonged in vitro islet culture. *Transplantation* 72:1730-1736, 2001).

In addition, two recent studies (Rutsky, et al. Microgravity culture condition reduces immunogenicity and improves function of pancreatic islets. *Transplantation* 74:13-21, 2002; Rutsky et al. Microgravity culture conditions decrease immunogenicity but maintain excellent morphology of pancreatic islets. *Transplant. Proc.* 33:388, 2001) compared mouse islets cultured in a Rotating Cell Culture System (RCCS) manufactured by Synthecon, Inc., Houston, Tex. and in conventional culture dishes. Fresh islets survived less than 15 days when transplanted into streptozotocin diabetic mice; whereas islets cultured in the RCCS or the culture dishes survived for over 100 days after transplantation. Furthermore, only one-third to one-half the number of RCCS-cultured islets were required to maintain euglycemia in the diabetic mice than those cultured in the dishes, indicating that the RCCS-cultured islets either had a better rate of survival or functioned better after being transplanted.

A continuing need exists for improving the culturing of pancreatic islets to enhance the islet viability and improve the survival of transplanted islets.

SUMMARY OF THE INVENTION

The present invention is a method for maintaining high densities of pancreatic islets in culture, wherein the method includes pre-incubating pancreatic islets with a laminin A chain peptide or a peptide containing an IKVAV domain.

One aspect of the invention is a method for increasing pancreatic islet viability for islet transplantation including: incubating a set of pancreatic islets with a quantity of a laminin A chain peptide containing the sequence of SEQ ID NO. 2; and culturing the pancreatic islets.

Another aspect of the present invention is a method for preventing pancreatic islet aggregation including: obtaining a set of human pancreatic islets from a pancreas; incubating the set of pancreatic islets with a quantity of a laminin A chain peptide containing the sequence of SEQ ID NO. 2; and culturing the pancreatic islets in a rotating cell culture system.

Yet another aspect of the present invention is a method for preventing pancreatic islet aggregation including: obtaining a set of human pancreatic islets from a pancreas; incubating the set of pancreatic islets with a quantity of a laminin A chain peptide containing the sequence of SEQ ID NO. 1 and variants thereof that inhibit the aggregation of pancreatic islets in culture; and culturing the pancreatic islets in a rotating cell culture system.

The foregoing has outlined several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed might be readily utilized as a basis for modifying or redesigning the method or process for carrying out the same purposes as the invention. It should be realized that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1A:
FIG. 1A-C shows the effect of preincubating pancreatic islets with a IKVAV-containing laminin A chain peptide.

Studies on mice pancreatic islets have compared pancreatic islets cultured in both a Rotating Cell Culture System (RCCS) and the conventional culture dish. The RCCS-cultured islets resulted in better islet transplants in at least two ways: 1) the RCCS-cultured islets maintained normal serum glucose levels in recipient mice for a longer period of time than the dish-cultured islets, and 2) diabetic animals were cured of their diabetes with fewer RCCS-cultured islets than were required for the dish-cultured islets. These results indicate that the transplanted RCCS-cultured islets were healthier and more viable than the dish-cultured islets.

Despite the advances in culturing islets, islet transplantation is faced with other difficulties that must be overcome if this procedure is to become a standard treatment for diabetes is humans. One major problem in using human pancreatic islets to treat diabetes has been the inability to maintain RCCS-cultured islets at sufficiently high densities for human transplants.

In the past, pancreatic islets cultured in high densities have become anoxic and died. For example, the maximum density of the islets that are successfully cultured in the RCCS bioreactor has been about 80 islets/ml. Although this density of islets is suitable for islet transplants in mice, human islet transplants require a much larger density of islets to be practical. The number of islets needed for human islet transplants ranges from about 400,000 to about 1,000,000 islets.

In the past a human cadaver pancreas yielded about 200,000 islets, so that the islets from two pancreases were generally needed for human islet transplants. Today a human cadaver pancreas can yield about 450,000 islets. If the transplantation of human pancreatic islet is to become a standard procedure, it is important that the islets isolated from a single pancreas be cultured in sufficient densities for sufficient periods of time to provide successful islet transplants the majority of the time.

When islets are cultured in a serum-free media for one month, the islets apparently at least partially recover from the trauma caused by the isolation process since the cultured islets provide improved islet graft survival after transplantation (Gaber, et al. Improved in vivo pancreatic islet function after prolonged in vitro islet culture. *Transplantation* 72:1730-1736, 2001). As noted above, two recent studies (Rutsky, et al. Microgravity culture condition reduces immunogenicity and improves function of pancreatic islets. *Transplantation* 74:13-21, 2002; Rutsky et al. Microgravity culture conditions decrease immunogenicity but maintain excellent morphology of pancreatic islets. *Transplant. Proc.* 33:388, 2001) have indicated that culturing islets in a RCCS provides healthier islets than culturing the islets in conventional culture dishes.

Unfortunately, whenever human pancreatic islets have been cultured in the RCCS at densities greater than 80 islets/ml, the islets have aggregated and become anoxic and died. In fact, researchers have noted that when human islets are cultured in the RCCS at high densities that the islets will occasionally form a single large cluster of dead islets. Since the RCCS is used in tissue engineering applications to promote the aggregation of cells, the observed islet clumping is not totally unexpected. However, successful high-density islet cultures must be able to inhibit the aggregation and death of islets in culture.

It has been estimated that for human islet transplants to be successful islet cultures having a density of about 400 islets/ml are necessary. Thus, the density of islets cultures must be increased approximately five fold to make human islet transplantation feasible as a standard procedure.

The present invention relates to a process for preventing or inhibiting the aggregation of pancreatic islets. Although the exact mechanism of action is not fully understood, it is thought that islet aggregation can be inhibited by interfering with the interaction of adhesion molecules found on the outer layer of islet cells and remnants of the extracellular matrix adhering to the islets after the enzymatic digestion of the pancreas.

Typically, the extracellular matrix is made up of a locally secreted network of proteins and polysaccharides that remain associated with the cells that synthesized them. The extracellular matrix of different cells exhibits tremendous variation; however, it is generally composed of fibrous proteins and polysaccharide glycosaminoglycans. The most common fibrous proteins are both structural proteins such as collagen and elastin and multi-adhesive proteins such as fibronectin and laminin.

Although little is known about the composition and structure of the extracellular matrix of pancreatic islet cells, the islet cell matrix has been reported to contain collagen IV, laminin, and fibronectin (Van Deijnen, J. H. M., et al., Significance of the peri-insular extracellular matrix for islet isolation from the pancreas of rat, dog, pig and man. *Cell Tissue Res.* 267:139-146, 1993).

The enzymatic digestion of the extracellular matrix during islet isolation has been reported to contribute to islet apoptosis (Thomas, F. T., et al. Extracellular matrix and apoptosis factors in isolated cell transplantation. *Surgery* 126:299-304, 1999). Cameron, et al. noted that the addition of a mixture of extracellular matrix proteins, added as the commercial product BD Matrigel™, enhanced the adherence of sertoli cells to the islets and improved glucose-stimulated insulin secretion in vitro (Cameron, D. F., et al. Formation of insulin-secreting, sertoli-enriched tissue constructs by microgravity coculture of isolated pig islets and rat sertoli cells. *In Vitro Cell. Dev. Biol.-Animal* 37:490-498, 2001). The major components of BD Matrigel are laminin, collagen, heparan sulfate proteoglycans, and entactin. Furthermore, extracellular matrix components, such as laminin, have been associated with maintaining the functional secretory response of pancreatic islets (Bosco, D., et al. Importance of cell-matrix interactions in rat islet β cell secretion in vivo. *Diabetes* 49:233-243, 2000). The mechanism of action of this observation is unknown.

The interaction of cells includes multiple interactions in a complicated series of events. To inhibit islet aggregation a number of possible approaches were considered. One approach was based on the hypothesis that the aggregation of islets at high densities was a result of normal interactions of cell surface adhesion molecules on the surface of islets and remnants of extracellular matrix on other islets.

The addition of extracellular proteins such as collagen, fibronectin, and laminin was initially considered as a means to inhibit the interaction of cell surface adhesion molecules on the islet surface and remnants of extracellular matrix on other islets. However, the addition of these proteins was problematic due to the probability that the proteins might actually increase islet aggregation. In addition, the proteins were purified from biological sources and would be difficult to get approved for standard clinical procedures. Therefore a number of small, chemically synthesized peptides known to bind to different integrins or other cell surface matrix-binding molecules were investigated.

For example, one set of experiments was performed to test four peptides derived from laminin and collagen for their ability to prevent the interaction of adhesion molecules to laminin or laminin by-products left by the islet isolation procedure and thereby block islet aggregation. Of the four peptides tested only the 19 amino acid synthetic peptide known as PA22-2 containing residues 2091-2108 of the laminin A chain showed substantial aggregation inhibiting activity when added to RCCS-cultured islets having a cell density of about 200-300 islets/ml. The PA22-2 peptide has the structure set forth below (Kleinman, et al. Identification of a 110-1Da Nonintegrin Cell Surface Laminin-Binding Protein which Recognizes an A Chain Neurite-Promoting Peptide. *Archives of Biochemistry and Biophysics* 290(2):320-325, 1991; Yamada et al. Laminin A Chain Deduced Amino Acid Sequence Expression Vectors and Active Synthetic Peptides. U.S. Pat. No. 5,211,657):

```
                                        SEQ ID No. 1
CYS-SER-ARG-ALA-ARG-LYS-GLN-ALA-ALA-SER-ILE-LYS-

VAL-ALA-VAL-SER-ALA-ASP-ARG
```

One domain of the PA22-2 peptide that is known to promote the differentiation of neurons from enteric crest-derived precursors has the structure set out below (Chalazonitis, et al. The $\alpha_1$ Subunit of Laminin-1 Promotes the Development of Neurons by Interacting with LBP110 Expressed by Neural Crest-Derived Cells Immunoselected from the Fetal Mouse Gut):

```
    ILE-LYS-VAL-ALA-VAL          SEQ ID No. 2
```

It is hypothesized that synthetic peptides containing the IKVAV peptide sequence (SEQ ID NO. 2) can inhibit the aggregation of islets cultures in the RCCS bioreactor. Experiments were performed to compare the aggregation of about 200-300 islets/ml cultured in the presence and absence of each peptide to be tested. Initial experiments added the peptide to the culture media in a small (10 ml) RCCS bioreactor vessel. It was realized that providing a large volume of culture media with sufficient concentrations of the PA22-2 peptide or another IKVAV-containing peptide component of laminin would be prohibitively expensive. Thus, the experimental protocol was altered as described below.

Peptide Treatment of Islet Cells

Human pancreatic islets were obtained from Islet Resource Centers or from Dr. Jose Oberholzer of the Division of Transplantation, Department of Surgery, University of Illinois. The islets were generally received within 24-36 hours after isolation from the pancreas. Upon receipt of the each batch of islets, the islets were divided into various samples and the viability and health one of the samples (Sample 1) was assessed by measuring the amount of aggregation, apoptosis and ATP levels in the islets.

In each sample, the islets were allowed to settle at 1×g in a sterile centrifuge tube. Once the islets had settled, the supernatant was removed and replaced with 2 ml of media. Control samples of islets (Samples 2 and 4) were placed in the control media (i.e., CMRL-1066 media containing 10% bovine serum, 1% penicillin/streptomycin/amphotericin B, and 2 mM glutamine) and experimental samples of islets (Samples 3 and 5) were incubated with the control media to which 50 µg/ml IKVAV-containing peptide such as the PA22-2 (SEQ ID NO. 1) peptide had been added. The IKVAV-containing peptides are hereinafter referred to as laminin A chain peptide.

All four samples were gently mixed and placed in a humidified incubator for 3 hours at 37° C. At half hour intervals, the tubes containing the samples were gently inverted to prevent aggregation of the islet pellet. After 3 hours, the media was removed from all the samples and replaced with fresh control media that did not contain the laminin A chain peptide. The laminin A chain peptide was only preincubated with the cells because it was found that leaving the peptide in the media during the entire culture period caused the petri dish control islets to adhere to the non-stick petri dishes and made it impossible to perform in vitro assays on the cells.

Samples 2 and 3 were transferred to standard culture dishes (petri dishes) at a cell density of approximately 200 islets/ml. Samples 4 and 5 were transferred to 35 ml perfused RCCS bioreactor vessels at a cell density of approximately 200 islets/ml. All of the samples (Samples 2-5) were then cultured for 7 days. After the Samples 2-5 had been cultured for 7 days, the islets were removed from the culture dish or RCCS bioreactor vessel and assessed for aggregation, apoptosis and ATP levels.

Figure 2A:
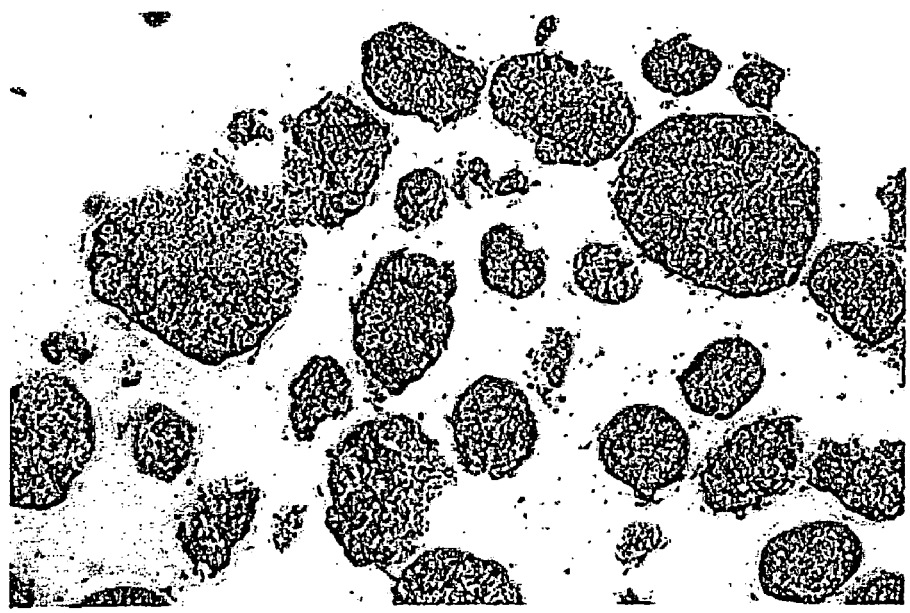
FIG. 2A-B shows stained thin sections of human pancreatic islets cultured for 7 days in a petri dish (A) or in a rotating cell culture system (B) where the islets were preincubated with an IKVAV-containing laminin A chain peptide.
Figure 2B:
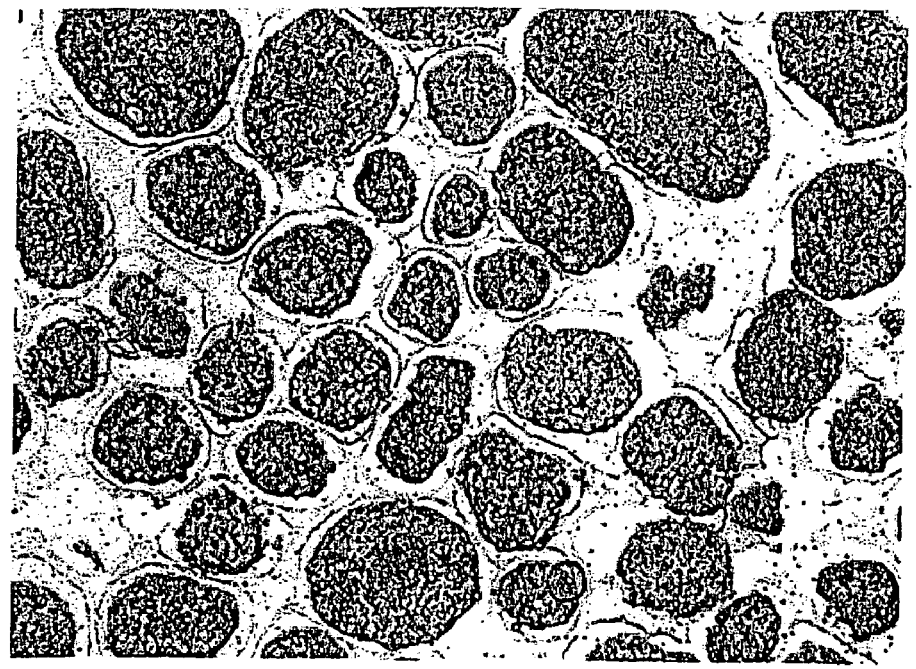

Occasionally, human islet preparations in the petri dish control samples (Samples 2 and 3) appeared to be breaking down during the seven-day culture period, probably due to overdigestion during the harvesting of the islets from the pancreas. However, islets from the same batch of islets (Sample 5) cultured in the RCCS bioreactor that had been preincubated with the laminin A chain peptide maintained a normal structure as shown in FIG. 2. FIG. 2 shows H & E stained thin sections of human islets. FIG. 2A illustrates the fragility of islets cultured for seven days in a petri dish, where a number of the cell membranes appear to be breaking down. FIG. 2B illustrates islets cultured in an RCCS bioreactor that had been preincubated with the laminin A chain peptide PA22-2 as described below. In contrast to the petri dish control samples shown in FIG. 2A, the RCCS cultured islets that had been preincubated in the laminin A chain peptide maintained their membrane integrity and appeared to be healthy and viable.

Aggregation

The aggregation of pancreatic islets observed in high density cultures invariably led to large numbers of the islets becoming anoxic and dying. As one object of the present invention was to decrease the aggregation of islets in such high-density cultures, Samples 2 through 5 were assessed (as described below) for the degree of aggregation that the islets in those samples underwent in culture when preincubated with or without the laminin A chain peptide.

An aliquot of islets from each sample was fixed by washing the islets two times in phosphate buffered saline (PBS) and then transferring the washed samples to a 4% paraformaldehyde solution for 2 hours to fix the islets. The fixed islets were rinsed with PBS and transferred into a 75% ethanol solution and stored at 4° C. The fixed islets were placed in a multiwell plate and examined under a microscope equipped with a digital camera. The islets were analyzed for their, degree of aggregation by digitizing ten microscopic fields and measuring the cross sectional areas of the islets within each field with the image processing program NIH Image.

The experimental results indicated that the RCCS-cultured islets exhibited a lower degree of aggregation when they had been preincubated with the laminin A chain peptide PA22-2.

One set of experiments preincubated human islets at a density of 300 islets/ml in the presence or absence of the laminin A chain peptide PA22-2. The results of this experiment are shown in FIG. 1. The human islets were preincubated in media with or without 50 µg/ml of the laminin A chain peptide for 3 hours in a humidified $CO_2$ incubator at 37° C. followed by a seven-day culture in an RCCS bioreactor or a petri dish.

Figure 1B:
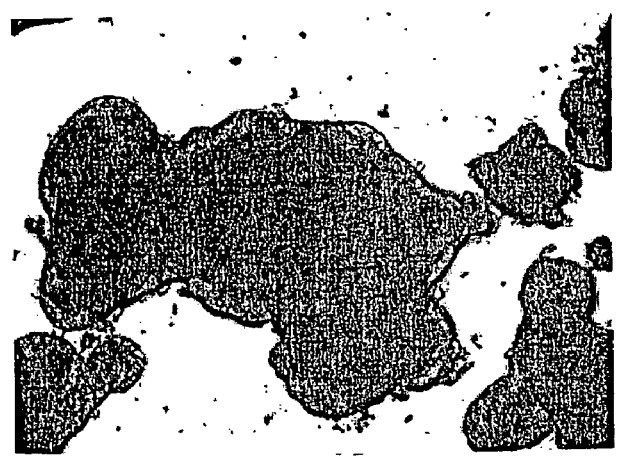
Figure 1C:
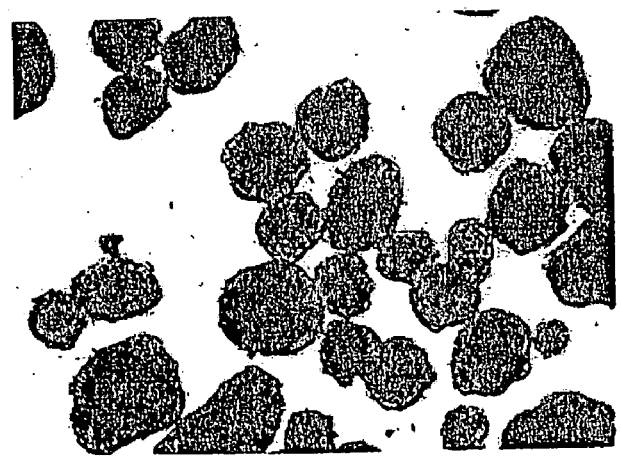

FIG. 1A illustrates islet cells incubated in a petri dish without the laminin A chain peptide (control islets). The islet cells were not aggregated after the seven-day culture in the petri dish. In contrast, FIG. 1B illustrates islet cells incubated in the RCCS bioreactor without being preincubated with the laminin A chain peptide. These islet cells aggregated and formed significant clumps of cells. FIG. 1C, on the other hand, illustrates islet cells that had been preincubated with the laminin A chain peptide before being incubated in the RCCS bioreactor for seven days. Exposure of the islets to the laminin A chain peptide for 3 hours was sufficient to prevent aggregation of the islets in the RCCS bioreactor, while allowing the petri dish control islets to remain in suspension. Thus, the laminin A chain peptide PA22-2 is thought to bind to its cell surface receptor with high affinity and is not dissociated from that receptor after the cells are washed.

However, the present invention of inhibiting the aggregation of islets in the RCCS bioreactor may preincubate the islets with an IKVAV-containing laminin A chain peptide for various periods of time, or may culture the islets in the RCCS in the presence of IKVAV-containing laminin A chain peptide throughout the culture period.

Apoptosis

Pancreatic islet apoptosis has been reported as a prognosticator of islet apoptosis and graft failure. Thus, apoptosis was measured in the cultured islets as an indicator of islet health and viability. A number of assays for apoptosis have been used to quantitate the degree of apoptosis in a cell sample. Some assays, such as the TUNEL and DNA fragmentation assays, detect apoptosis late in the process. More recent assays, such as the caspase 3 assay used for these experiments, have been shown detect apoptosis early in the process. Caspase 3 is reported to be an important early step in the initiation of apoptosis in islets (Cattan, P., et al. Early assessment of apoptosis in isolated islets of Langerhans. *Transplantation* 71:857-862, 2001).

The islets in each sample (Samples 2-5) were assayed for their caspase 3 activity. The islets were removed from their respective culture plate or RCCS bioreactor, rinsed with phosphate buffered saline (PBS), centrifuged into a pellet and stored frozen until the caspase 3 assays were run.

At the time of caspase 3 analysis, the islets were thawed and lysed for 30 min with a buffer containing 10 mM Tris pH 7.5, 100 mM NaCl, 1 mM EDTA, and 0.01% Triton X-100 at 0° C. The lysed cells were centrifuged at 5,000 rpm for 5 minutes in a microcentrifuge.

Fifty microliters of the lysed cell supernatant from each sample was transferred into a microplate well. A solution of substrate, containing a peptide linked to rhodamine, was added to each microplate well containing the lysed cell supernatant. The lysed cell supernatant and substrate were incubated at room temperature for 30 min. Active caspase 3 in the supernatant samples cleaved the peptide from the rhodamine. The free rhodamine was measured by fluorescence (excitation/emission-496/520 nm). The fluorescence was quantitated using arbitrary fluorescence units derived by normalizing the rhodamine fluorescence to the quantity of DNA in the islet sample, which is directly proportional to cell number.

Figure 3:
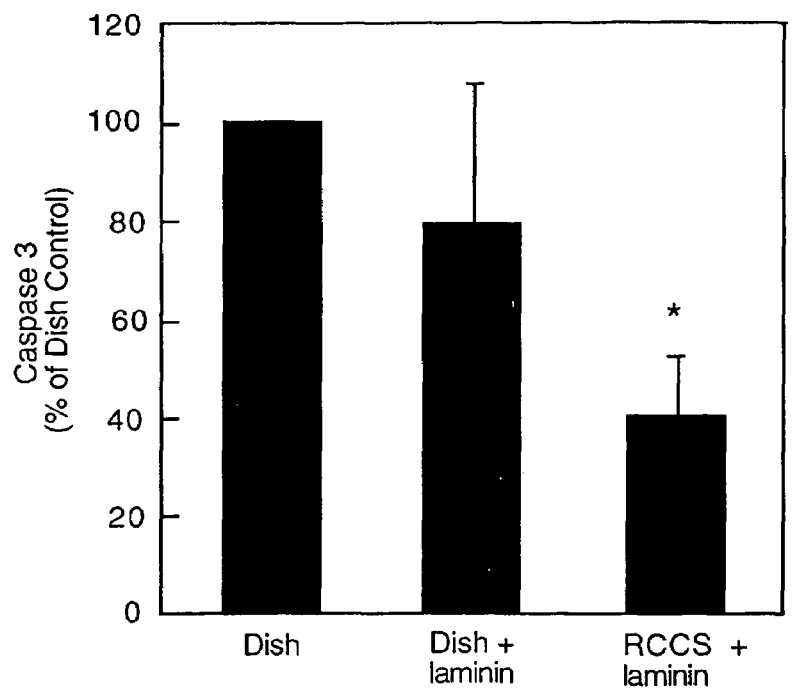
FIG. 3 shows the caspase 3 activity in cultured human pancreatic islets that were or were not preincubated with an IKVAV-containing laminin A chain peptide.

Experiments were performed to compare islet caspase 3 activity in islets cultured in conventional petri dishes (labeled in FIG. 3 as Dish) with islets preincubated with the laminin A chain peptide PA22-2 and cultured in an RCCS bioreactor (labeled in FIG. 3 as RCCS+ laminin). Sample 1 containing fresh islets had a low level of caspase 3 activity. As shown in FIG. 3, Sample 2 (labeled Dish), consisting of islets cultured in a petri dish without being preincubated with the laminin A chain peptide PA22-2 was taken as the control or 100% caspase 3 activity. A petri dish culture of islets that had been preincubated for 3 hours with 50 µg/ml of the laminin A chain peptide (labeled in FIG. 3 as Dish+ laminin) was also examined to determine if the laminin A chain peptide alone had any effect on apoptosis. The data from four experiments was analyzed by a one-way ANOVA. Differences between the groups were determined by the Student-Newman Keuls test. A significant difference from the Dish control were marked with an * and had a p value less than 0.05 (n=4). As shown in FIG. 3, the Dish+ laminin samples tended to have a slightly lower caspase 3 activity but the values did not have a p value less than 0.05 and were thus not considered significantly different.

In contrast, the RCCS-cultured islets of Sample 5, preincubated for 3 hours in the presence of 50 µg/ml laminin A chain peptide PA22-2, had less caspase 3 activity than the RCCS-cultured islets of Sample 4 that were not preincubated with the laminin A chain peptide (not shown in FIG. 3). The RCCS+ laminin islets had significantly less caspase 3 activity than did the dish-cultured islets.

These data show that culturing human islets in the RCCS can significantly reduce apoptosis as measured by caspase 3 activity. The laminin A chain peptide PA22-2, by itself appeared to have no significant effect on islet caspase 3 activity, but is beneficial in preventing islet aggregation in islets cultured in the RCCS bioreactor.

ATP Assay

ATP has also been reported as an important determinant of the condition of isolated islets (Brandhorst, D. et al. Large variability of the intracellular ATP content of human islets isolated from different donors. *J. Mol. Med.* 77:93-95, 1999). The higher the ATP levels the better. In fact, islet ATP levels are considered by some investigators to be the best prognosticator of islet transplant success.

Islet ATP levels were measured by luciferin/luciferase luminescence. Frozen islets were lysed in PBS by freeze thawing the islet samples. The cells were pelleted by centrifugation and 10 µl of the lysed cell supernatant was placed in a luminescence multiwell plate with 90 µl of reaction solution (25 mM Tricine pH 7.8, 5 mM $MgSO_4$, 0.1 mM EDTA, 0.1 mM sodium azide with 0.5 mM lucifirin, 1 mM DTT and 12.5 µg of firefly luciferase). The plates were incubated at 28° C. for 15-30 minutes and the luminescence measured in a luminometer. The luminescence of the islets was normalized to the quantity of DNA in the islet sample, wherein the quantity of DNA is directly proportional to the number of islets present.

The data from four experiments was analyzed by a one-way ANOVA. Differences between the groups were determined by the Student-Newman Keuls test. A significant difference from the Dish control were marked with an * and had a p value less than 0.05 (n=4).

Figure 4:
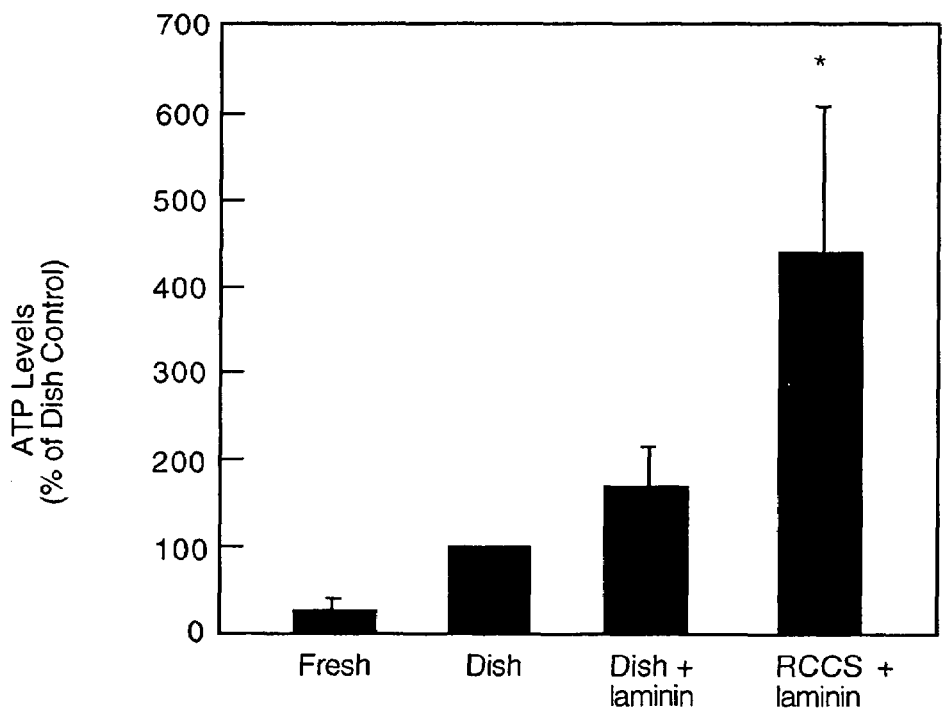
FIG. 4 shows the ATP levels in cultured human pancreatic islets that were or were not preincubated with an IKVAV-containing laminin A chain peptide.

As shown in FIG. 4, the Sample 1 containing fresh islets had very low levels of ATP, which is thought to account for the lack of success seen in transplanting fresh islets. As expected the islets of Sample 2, cultured in a culture dish in the absence of the laminin A chain peptide, had significant quantities of ATP approaching 400 units and were taken as the control value or 100% in FIG. 4. The islets of Sample 3, preincubated for 3 hours with 50 µg/ml of the laminin A chain peptide PA22-2 and cultured in the petri dish, tended to have higher ATP levels but the values did not have a p value less than 0.05 and were thus not considered significantly different.

On the other hand, the RCCS-cultured islets of Sample 5 that had been preincubated in the presence of the laminin A chain peptide (labeled in FIG. 4 as RCCS+laminin) had significantly higher ATP levels than the islets in the Dish control (Sample 2). Thus, the pretreatment of pancreatic islets with the laminin A chain peptide PA22-2 improves the ATP levels of the islets above that of fresh islets or islets cultured in static petri dish cultures.

Although the present invention and its advantages have been described in detail, it should be understood that various changes, substitutions and alterations can be made herein without departing from the spirit and scope of the invention as defined by the appended claims. For example, a number of IKVAV-containing laminin A chain peptides can be synthesized and used to inhibit the aggregation of pancreatic islets in the RCCS bioreactor.

What is claimed is:

1. A method for increasing human pancreatic islet viability for islet transplantation including:
   incubating a set of human pancreatic islets with a quantity of a laminin A chain peptide consisting of the sequence of SEQ ID NO:1; and
   culturing the pancreatic islets in a rotating cell culture system.

2. The method of claim 1, further comprising washing the pancreatic islets before culturing the islets.

3. The method of claim 1, wherein the islets are incubated with the laminin A chain peptide for at least 3 hours.

4. The method of claim 1, wherein the islets are incubated in about 50 µg/ml of the Laminin A chain peptide.

5. The method claim 1, wherein the pancreatic islets are cultured in the rotating cell culture system at a cell density of about 200 islets per milliliter or greater.

6. The method of claim 1, wherein the pancreatic islets are cultured in the rotating cell culture system for about seven days or more.

7. A method for inhibiting in vitro pancreatic islet aggregation including:
   obtaining a set of human pancreatic islets from a pancreas;
   incubating the set of pancreatic islets with a quantity of a laminin A chain peptide consisting of the sequence of SEQ ID NO:1; and
   culturing the pancreatic islets in a rotating cell culture system.

8. The method of claim 7, wherein the islets are incubated with the laminin A chain peptide for at least 3 hours.

9. The method of claim 7, wherein the pancreatic islets are cultured in the rotating cell culture system for at least seven days.

10. The method of claim 7, wherein the pancreatic islets are cultured in the rotating cell culture system at a cell density of about 200 islets per milliliter or greater.

11. The method of claim 7, further comprises washing the pancreatic islets with media before culturing the islets in the rotating cell culture system.

* * * * *

UNITED STATES PATENT AND TRADEMARK OFFICE
CERTIFICATE OF CORRECTION

| | |
|---|---|
| PATENT NO. | : 7,507,581 B2 |
| APPLICATION NO. | : 11/396437 |
| DATED | : March 24, 2009 |
| INVENTOR(S) | : Stephen S. Navran, Jr. |

It is certified that error appears in the above-identified patent and that said Letters Patent is hereby corrected as shown below:

Insert new section header at Column 1, Line 16: --STATEMENT REGARDING FEDERALLY SPONSORED RESEARCH OR DEVELOPMENT--

Insert new paragraph under new section header: --Research leading to this invention was federally supported, in part, by the Small Business Innovation Research Program, National Institutes of Health, through grants 1R41DK064424-01A1 and 2R42DK064424-02A2, and the U.S. Government has certain rights hereunder in this invention.--

Signed and Sealed this

Twenty-third Day of March, 2010

David J. Kappos
*Director of the United States Patent and Trademark Office*